United States Patent
Kaikenger (10) Patent No.: US 10,549,065 B2
(45) Date of Patent: Feb. 4, 2020

(54) PATIENT SUPPORT SYSTEM FOR MONITORING AND CONTROLLING SLEEP

(71) Applicant: Hill-Rom SAS, Pluvigner (FR)

(72) Inventor: Philippe Kaikenger, Pluvigner (FR)

(73) Assignee: Hill-Rom SAS, Pluvigner (FR)

( * ) Notice: Subject to any disclaimer, the term of this patent is extended or adjusted under 35 U.S.C. 154(b) by 419 days.

(21) Appl. No.: 15/176,987

(22) Filed: Jun. 8, 2016

(65) Prior Publication Data
US 2016/0375219 A1 Dec. 29, 2016

(30) Foreign Application Priority Data

Jun. 24, 2015 (EP) .................................... 15305981

(51) Int. Cl.
*A61M 21/00* (2006.01)
*A61G 7/005* (2006.01)
(Continued)

(52) U.S. Cl.
CPC ........... *A61M 21/00* (2013.01); *A61B 5/0022* (2013.01); *A61B 5/024* (2013.01); *A61B 5/0816* (2013.01); *A61B 5/11* (2013.01); *A61B 5/4812* (2013.01); *A61B 5/6891* (2013.01); *A61G 7/00* (2013.01); *G16H 40/20* (2018.01);
(Continued)

(58) Field of Classification Search
CPC .......... A61M 21/02; A61M 2021/0027; A61M 2021/0044; A61M 2021/005; A61M 2230/06; A61M 2230/42; A61M 2230/63; A61G 7/05; A61G 2007/0524; A61B 5/11; A61B 5/4812; A61B 5/4815; G06F 19/30
See application file for complete search history.

(56) References Cited

U.S. PATENT DOCUMENTS 6,350,275 B1 2/2002 Vreman et al.
6,669,627 B1 12/2003 Campbell et al.
(Continued)

FOREIGN PATENT DOCUMENTS

WO WO 2012156654 A1 * 11/2012 ............ A61M 21/02

OTHER PUBLICATIONS

Machine Translation of WO 2012156654 A1.*
(Continued)

*Primary Examiner* — David J. McCrosky
(74) *Attorney, Agent, or Firm* — Barnes & Thornburg LLP (57) ABSTRACT

A patient support system includes a patient support apparatus having a base frame and a patient support surface. A network includes one or more of such patient support systems and an associated computer device. The patient support system includes: at least one sensor configured to detect at least one patient characteristic; at least one light emitting device capable of emitting light in at least a first range of visible wavelengths; and a controller configured to: receive the or each output from the at least one sensor; determine a stage of sleep of a patient on the patient support surface; receive a wake-up signal; and after receipt of the wake-up signal, activate the or each light emitting device to emit light substantially only in the first range of visible wavelengths when the controller next determines that the patient is in a light stage of sleep. The associated computer device is configured to carry out a patient wake-up process.

20 Claims, 4 Drawing Sheets

(51) Int. Cl.
  *A61B 5/00*   (2006.01)
  *G16H 40/20*  (2018.01)
  *A61B 5/024*  (2006.01)
  *A61B 5/08*   (2006.01)
  *A61B 5/11*   (2006.01)
  *A61G 7/00*   (2006.01)

(52) U.S. Cl.
  CPC ............... *A61M 2021/005* (2013.01); *A61M 2021/0027* (2013.01); *A61M 2021/0083* (2013.01)

(56) References Cited

U.S. PATENT DOCUMENTS

| | | | |
|---|---|---|---|
| 7,248,915 B2 | 7/2007 | Ronnholm et al. | |
| 7,956,756 B2 | 6/2011 | Kubey et al. | |
| 8,579,795 B2* | 11/2013 | Martel | A61M 21/02 307/10.8 |
| 2005/0143617 A1* | 6/2005 | Auphan | A61B 5/08 600/26 |
| 2005/0248962 A1 | 11/2005 | Searfoss | |
| 2006/0089546 A1 | 4/2006 | Mahony et al. | |
| 2007/0002692 A1 | 1/2007 | VanBrunt | |
| 2007/0118026 A1 | 5/2007 | Kameyama et al. | |
| 2007/0136098 A1* | 6/2007 | Smythe | A61N 1/37264 705/3 |
| 2013/0253951 A1* | 9/2013 | Richter | G06F 19/3418 705/3 |
| 2013/0342351 A1 | 12/2013 | Riley et al. | |

OTHER PUBLICATIONS

Martin, M. "Daily App: Morning Sun is a free alarm clock for iOS with some unique features" Engadget.com. May 26, 2014. Retrieved from <https://www.engadget.com/2014/05/26/daily-app-morning-sun-is-a-free-alarm-clock-for-ios-with-some-u/> (Year: 2014).*

Internet Archive, "Morning Sun" Picobrothers.com. May 30, 2014. Retrieved from <https://web.archive.org/web/20140530165239/http://morningsun.picobrothers.com/> (Year: 2014).*

NP100 Prevention Surface Brochure dated Sep. 25, 2008 (2 pages).

AccuMax Quantum™ VPC Mattress Brochure dated May 13, 2015 (8 pages).

Non-Powered Surfaces Portfolio Brochure dated Mar. 12, 2010 (4 pages).

Extended European Search Report, European Application No. 15305981.1, completed Dec. 16, 2015, (9 pages).

Scientific Information Summary NightCove™ dated Jul. 2011 (22 pages).

* cited by examiner

PATIENT SUPPORT SYSTEM FOR MONITORING AND CONTROLLING SLEEP

The present application claims priority, under 35 U.S.C. § 119(a), of European Application No. 15305981.1 which was filed Jun. 24, 2015 and which is hereby incorporated by reference herein.

BACKGROUND

The present disclosure relates to a patient support system, comprising a patient support apparatus, and associated system for monitoring and controlling the sleep of patients. Such person support apparatuses include mattresses, cushions, beds, stretchers, chairs, wheelchairs, tables, and other similar devices. Person support apparatuses of this type may be found, for example, in healthcare facilities, homes, and other locations in which care is provided. The present disclosure is particularly relevant to use in healthcare facilities.

Currently, patient support apparatuses having monitoring systems that detect relatively large-scale movements, or the lack thereof, of a person relative to a person support apparatus. These systems may be used to detect whether the person is about to exit the bed, or the like. Further, some existing systems monitor the physiological activity of a person (e.g. heart rate, breathing rate) while the person is positioned on a person support apparatus. Other systems such as patient wearable systems are known. These systems are able to detect very slight movements (such as a heartbeat or the rise and fall of a person's chest). These systems are often used to detect the onset of adverse events related to a person's health. Still further systems exist that use the outputs of such monitoring systems to determine the sleep quality of the person, and enable subsequent adjustments to the sleep process or person support apparatus settings.

It is well-known that sleep is required to aid physical repair of the body, and that particular stages of sleep are more effective in enabling such repair. It is believed that few, if any, patient support systems exist that are directed to monitoring and improving the sleep and wake-up experience of patients, in particular while those patients are in a healthcare facility.

It would therefore be of benefit to provide a system which improves the sleep and wake-up experience of patients situated on a person support apparatus. It would also be of benefit to provide a system which enables remote control of the patient support apparatus.

SUMMARY

According to one aspect of the present disclosure, there is provided a patient support system comprising a patient support apparatus having a base frame and a patient support surface. The system comprises: at least one sensor coupled to the patient support apparatus, configured to detect at least one of: patient movement; patient breathing rate; and patient heart rate; at least one light emitting device capable of emitting light in at least a first range of visible wavelengths between about 440 nm and about 490 nm; and a controller. The controller is configured to: receive the or each output from the at least one sensor; determine a stage of sleep of a patient on the patient support surface in dependence on the or each received output; receive a wake-up signal; and after receipt of the wake-up signal, activate the or each light emitting device to emit light substantially only in the first range of visible wavelengths when the controller next determines that the patient is in a light stage of sleep.

According to this disclosure, providing a patient support system which determines the stage of sleep of a patient on the patient support surface, and then subsequently activating a light emitting device which emits lights within a specific range of wavelengths enables the patient to be woken from sleep in an efficient manner which reduces the effects of, for example, sleep inertia and makes it easier for a person to awake from sleep. Sleep inertia describes the state of a person being awake but not having fully recovered physical and/or cognitive abilities.

It has been found that providing the user with light stimulus having wavelengths between about 440 nm and about 490 nm is effective at suppressing melatonin synthesis. Melatonin is well-known as a major factor in controlling the body's circadian rhythm and therefore controlling sleep. As such, providing a light stimulus which suppresses melatonin synthesis when the patient is in a light stage of sleep results in the patient induces the patient to wake-up.

As used herein, the term "stage of sleep" refers to the set of sleep stages including: awake; stage 1; stage 2; stage 3; stage 4; and REM (rapid eye movement). The term "light stage of sleep" refers to stages 1 and 2. Stages 3 and 4 are considered deep sleep. During sleep the body cycles through the various stages of sleep. Each stage of sleep is characterized by particular physical and physiological criteria which the at least one sensor of the patient support system is configured to detect, the controller being configured to determine the stage of sleep in dependence on the sensor output.

The at least one sensor may be further configured to detect body temperature.

The, or at least one of the, sensors may be provided in a wearable device, the device being configured to be worn by the patient.

The controller may be further configured to activate the or each light emitting device to emit light substantially only in the first range of visible wavelengths by progressively increasing the intensity of the light emitted by the or each light emitting device from a first intensity to a second intensity over a pre-determined period of time. In this way, the wake-up experience can be more progressive and natural, and thus the effects of sleep inertia can be further reduced.

In one embodiment, the or each light emitting device is capable of emitting light in at least a first range of visible wavelengths between about 450 nm and about 470 nm. This range of wavelengths has been found to be even more effective at melatonin suppression.

The controller may be further configured to deactivate the light emitting device when the determined sleep state has changed from light sleep to awake.

In a second embodiment, the at least one light emitting device may be further capable of emitting light in at least a second range of visible wavelengths greater than about 590 nm. In this second embodiment, the controller is further configured to: receive a sleep signal; and after receipt of the sleep signal, activate the or each light emitting device to emit light substantially only in the second range of visible wavelengths.

Providing light stimulus having a wavelength greater than about 590 nm has been found to reduce or avoid the suppression of melatonin synthesis. Therefore, advantageously, providing a light emitting device capable of emitting light having a wavelength greater than 590 nm promotes the onset of sleep.

In the second embodiment, the controller may be further configured to deactivate the or each light emitting device from emitting light in the second range of visible wavelengths when the controller determines that the patient is in a stage of sleep.

In the second embodiment, the sleep signal may be generated by the patient providing an input to the system. Alternatively, or in addition, the sleep signal may be transmitted to the patient support system from a remote device. Alternatively, or in addition, the sleep signal may be generated at a pre-determined time of day.

The wake-up signal may be at least one of: a signal generated at a pre-determined time of day; and a signal generated by a remote user request to wake-up the patient. The wake-up signal may be a combination of both a signal generated at a pre-determined time of day and a signal generated by a remote user request to wake-up the patient. Where the wake-up signal is a combination, the controller is optionally configured to only activate the light emitting device to emit light substantially only in the first range of wavelengths on receipt of both signals.

The pre-determined time of day may be set by the patient, or by a remote user. The signal may be generated by a clock integral to the patient support apparatus, or by a clock remote from the patient support apparatus. The signal may be generated by a timer integral to the patient support apparatus, or by a timer remote from the patient support apparatus.

The or each light emitting device may comprise light emitting diodes tuned to the required range of wavelengths. The light emitting device may comprise two sets of light emitting diodes, each set configured to the first and second range of wavelengths respectively. The or each light emitting device may comprise a filter. The filter may be a band-pass filter, for example having a band allowing wavelengths within the first range of wavelengths. The filter may be a high-pass filter, for example allowing all wavelengths above about 590 nm for the second range of wavelengths. The or each light emitting device may be any other suitable type of light emitting device, either alone or in combination with a suitable filter.

The or each light emitting device may be coupled to the base frame, adjacent a head-end of the patient support surface. The or each light emitting device may be coupled to one or more side rails of the base frame. The or each light emitting device may be coupled to a headboard of the base frame. In a contemplated embodiment, the patient support system comprises at least two light emitting devices, a first light emitting device coupled to a first side rail, and a second light emitting device coupled to a second side rail. Optionally, in this contemplated embodiment, the direction in which the patient is facing while asleep is not relevant, the patient will always have line of sight to at least one light emitting device.

The or each light emitting device may be mounted on the ceiling substantially directly above the patient support apparatus.

At least one light emitting device may be a display device. For example, the display device may be an LED (light emitting diode) display, LCD (liquid crystal) display, OLED (organic light-emitting diode) display, plasma display or any other suitable display. The display may in addition be used as a: computer screen; television screen; multimedia screen; or the like. The display may be coupled directly to the base frame. Alternatively, the display may be mounted on a wall adjacent the patient support apparatus.

The or each light emitting device, such as the display, may be mounted on a movable arm. The movable arm may comprise at least one actuator to move the display to a pre-determined position when the controller receives the wake-up signal. The actuator may be a motor, such as a stepper motor. The pre-determined position is optionally such that the display faces the head-end of the patient support apparatus. In this way, the patient or other user, such as a healthcare professional, does not have to position the display before the patient goes to sleep. The monitor and movable arm may comprise proximity sensors to sense the presence of nearby objects to prevent the monitor from impacting those objects.

As used herein, healthcare professional refers to a nurse, doctor, carer or other such type of person.

Where the patient support system comprises a display, the controller may be configured to color-adjust an image such that, when the color-adjusted image is displayed on the display device, the display substantially only emits light in the first range of wavelengths. Similarly, in the second embodiment, the controller may be configured to color-adjust an image such that, when the color-adjusted image is displayed on the display device, the display substantially only emits light in the light in the second range of wavelengths. Optionally, the image is color-adjusted such that the global shade of the images is such that the display emits light in the first range of wavelengths, or the second range of wavelengths.

The image color adjusted to the first range of wavelengths may be appropriate for the morning. For example, the image may be a sunrise. The image color adjusted to the second range of wavelengths may be appropriate for the evening. For example, the image may be a sunset.

The image may be a series of images to generate a moving image, such as a video.

The patient support system may comprise an input for receiving inputs from the patient and/or from a user, such as a healthcare professional. Where the patient support system comprises a display, the display may be a touchscreen for receiving the inputs.

The patient support system may further comprise a speaker, the controller being further configured to activate the speaker, to output sound conducive to waking up, when activating the or each light emitting device to emit light substantially only in the first range of visible wavelengths.

The patient support system may further comprise means for emitting smells, the controller being further configured to activate the means for emitting smells, to output smells conducive to waking up, when activating the or each light emitting device to emit light substantially only in the first range of visible wavelengths.

The patient support system may further comprise a temperature regulator to control the temperature of the patient support surface. The controller may be configured to activate the temperature regulator, on activating the light emitting device, to control the temperature of the patient support surface. The controller may be configured to raise the temperature of the patient support surface when activating the light emitting device to substantially only emit light in the second range of wavelengths. The temperature controller may be configured to raise the temperature by at least 1 degree Celsius, such as between about 1 degree Celsius and about 2 degrees Celsius.

The controller of the patient support system may comprise a processor, and associated memory. The logic, functions and processes identified herein as being conducted by the controller may be implemented as one or more separate modules that are in communication with the processor or may be entirely incorporated into the processor. Additionally, the processor itself may be implemented as a single module or a number of distributed modules.

The person support apparatus may further comprise a lower frame, supports or lift mechanisms coupled to the lower frame, and an upper frame movably supported above the lower frame by the supports. The lift mechanisms may be configured to raise and lower the upper frame with respect to the lower frame and move the upper frame between various orientations, such as, Trendelenburg and reverse Trendelenburg.

The upper frame may include an upper frame base, a deck coupled to the upper frame base, and a plurality of siderails. The deck may include a leg section, a thigh section, a seat section, and a head and torso section. The leg section and the thigh section may be considered to comprise a lower limb support section. The head and torso section may be considered to comprise an upper body support section. The leg section, the thigh section, and the seat section may be considered to comprise a lower body support section. At least the leg section, the thigh section, and the head and torso section are optionally movable with respect to one another and/or the upper frame base. The leg section, the thigh section, the seat section, and the head and torso section may cooperate to move the person support apparatus between a substantially planar or lying down configuration and a chair configuration. The leg section, the thigh section, the seat section, and the head and torso section may cooperate to move the person support apparatus between a substantially planar or lying down configuration and an angled or reclined configuration. The head and torso section may be moved such that it is at an angle of at least about 30° with respect to a reference plane passing through the upper frame.

The siderails may be configured to move between a deployed position and a storage position, and are used to locate the perimeter of the upper frame and assist with ingress/egress to/from the person support apparatus. The siderails may include a base, a movement mechanism movably coupled to the base, and a panel movably coupled to the movement mechanism.

The person support surface is configured to support a person thereon and move with the deck between the various configurations. The person support surface is a hospital bed mattress in some embodiments. The person support surface may include a heat and moisture regulating topper positioned on the mattress. The person support surface may include a pressure mapping mat positioned on the mattress. The pressure mapping mat may be used as at least one of the sensors used to determine the stage of sleep. The person support surface according to some embodiments includes a leg portion, a thigh portion, a seat portion, and a head and torso portion, which is supported on corresponding sections of the deck. The deck sections may help move and/or maintain the various portions of the mattress at angles $\alpha$, $\beta$ and $\gamma$ with respect to the reference plane.

The person support surface may be a non-powered (static) surface. Alternatively, the person support surface is a powered (dynamic) surface configured to receive fluid from a fluid supply.

The person support surface may include a mattress cover and a mattress core enclosed by the mattress cover. The mattress core can be composed of a single type of material or a combination of materials and/or devices. In the case of a powered surface, the mattress core optionally includes at least one fluid bladder therein that receives fluid from a fluid supply to maintain the fluid pressure within the fluid bladder at a predetermined level. The powered surface may include non-powered components, such as, a foam frame that at least one fluid bladder is positioned between. Wedge shaped bladders may be mirrored laterally about the centerline of the mattress and are optionally configured to be inflated consecutively to laterally tilt the occupant, thereby relieving pressure on various portions of the occupant's body to help reduce the occurrences of pressure ulcers.

In the case of a non-powered surface, the mattress core is optionally composed of a cellular engineered material, such as, single density foam. The mattress core may include at least one bladder, such as, a static air bladder or a static air bladder with foam contained there within, a metal spring and/or other non-powered support elements or combinations thereof. The mattress core may include multiple zones with different support characteristics configured to enhance pressure redistribution as a function of the proportional differences of a person's body. Also, in some embodiments, the mattress core includes various layers and/or sections of foam having different impression load deflection (ILD) characteristics, such as, in the NP 100 Prevention Surface, AccuMax Quantum™ VPC Therapy Surface, and NP200 Wound Surfaces sold by Hill-Rom®.

As will now be appreciated, any type of suitable patient support apparatus may be used in the present disclosure.

According to a further aspect of the present disclosure, there is provided a system for a healthcare facility, comprising: a plurality of patient support systems as described herein, each patient support system further comprising communications circuitry configured to communicate with a network; and a computer device remote from the patient support systems, comprising communications circuitry configured to communicate with the network. The computer device is configured to: receive an input from a user, such as a healthcare professional, to initiate a wake-up process; request stage of sleep data for each patient associated with each of the plurality of patient support systems; receive the stage of sleep data for each patient; send a wake-up signal to each patient support system where the associated patient is in a light stage of sleep; and indicate to the user the patient support systems which were sent a wake-up signal.

According to this disclosure, providing a remote computer device in communication with a plurality of patient support systems as described herein, enables the more efficient control of the sleep monitoring and control functions of multiple patient support systems. The remote computer device can centrally provide wake-up signals to the plurality of patient support systems, and thereby enable the patient support system to be simplified which reduces costs and manufacturing complexity.

The computer device may be further configured to periodically request stage of sleep data for each patient associated with each of the plurality of patient support systems until a wake-up signal has been sent to all of the plurality of patient support systems. In this way, the system ensures that all patients associated with the plurality of patient support systems are woken up. Alternatively, a wake-up signal may be transmitted to each patient support system at substantially the same time, independent of whether the associated patient is in a light stage of sleep. The light is then activated immediately. In this alternative, the controller of each patient support system may be configured to store in memory the wake-up signal, and only activate the light emitting device when the patient next enters a light stage of sleep.

The computer device is optionally further configured to indicate to the user the patient support systems where the associated patient's determined stage of sleep is awake. The indicator may be a light adjacent a patient support apparatus ID, and/or adjacent the name of the associated patient, and/or adjacent the room number where the patient support apparatus is located. The light may be colored, for example green, and may comprise indicia, such as the word "go" or "awake".

The computer device may be further configured to: determine a linear sequence, in which to attend the patients, in dependence on the stage of sleep data received from each patient support system, the sequence starting with the patient whose stage of sleep has been awake for the longest period of time; and indicate the sequence to the user.

The sequence may be updated as patients move from the light stage of sleep to the awake stage of sleep.

The remote computer device may comprise a controller, the controller configured to be the controller for each of the plurality of patient support systems. Providing a single central controller may yet further improve the efficiency of the system, and thereby reduce costs.

The communications circuitry is optionally configured to allow bi-directional communication. The communications circuitry may be configured to communicate with the network over a wired connection, or a wireless connection. The network may be an Ethernet network. The communications may be configured according to a TCP/IP or other suitable electronic communications protocol. Where the communications circuitry is configured to communicate via a wireless connection a wireless communication protocol, such as an 802.11g protocol, Bluetooth protocol, Zigbee protocol, and so on, may be used. In contemplated embodiments, the wireless communication protocol is wi-fi such as any of the 802.11 sub-protocols a/b/g/n/ac. The network may be a local area network (LAN) or a peer-to-peer network.

The remote computer device optionally comprises a processor, associated memory, and a display device.

The remote computer device may be further configured to store data relating to each patient associated with a patient support system. The data may comprise at least one of: previous time period between activation of light emitting device and patient waking up; average time period between activation of light emitting device and patient waking up; and maximum time period between activation of light emitting device and patient waking up. The remote computer device may be further configured to utilize the stored data as an input to determine a time to send the wake-up signal, such that the patients awake closer to a pre-determined time. The pre-determined time may be set by the patient, or by the user, such as a healthcare professional.

The remote computer device may be a workflow server, a nurse call station, or another healthcare facility related central computer system.

It will be appreciated that a healthcare facility, such as a hospital, will have multiple beds, such as patient support apparatuses as described herein. For each of those beds to communicate with remote computers and servers the hospital optionally has multiple network interface units (NIU) associated with the various beds. Each NIU is optionally mounted at a particular location in a hospital, or may be coupled directly to the bed. For example, one or more NIUs will be located in various patient rooms. Each bed and each NIU is optionally assigned a unique identification (ID) code, such as a serial number. In some embodiments, the remote computer device, such as a nurse call system, has software that operates to associate bed ID data with NIU ID data so that the system can keep track of which bed is located in each room of the hospital and convey this information to users, such as healthcare professionals. This information can be used to inform the healthcare professional which room each patient is in, and in which bed, and thus provides the healthcare professional with the sequence in which to attend the patients.

Any feature in one aspect of the disclosure may be applied to other aspects of the disclosure, in any appropriate combination. In particular, method aspects may be applied to apparatus aspects, and vice versa. Furthermore, any, some or all features in one aspect can be applied to any, some or all features in any other aspect, in any appropriate combination.

It should also be appreciated that particular combinations of the various features described and defined in any aspects of the disclosure can be implemented and/or supplied and/or used independently.

The disclosure extends to methods and apparatus substantially as herein described with reference to the accompanying drawings.

BRIEF DESCRIPTION OF THE DRAWINGS

The disclosure will be further described, by way of example only, with reference to the accompanying drawings in which.

DETAILED DESCRIPTION

Figure 1:
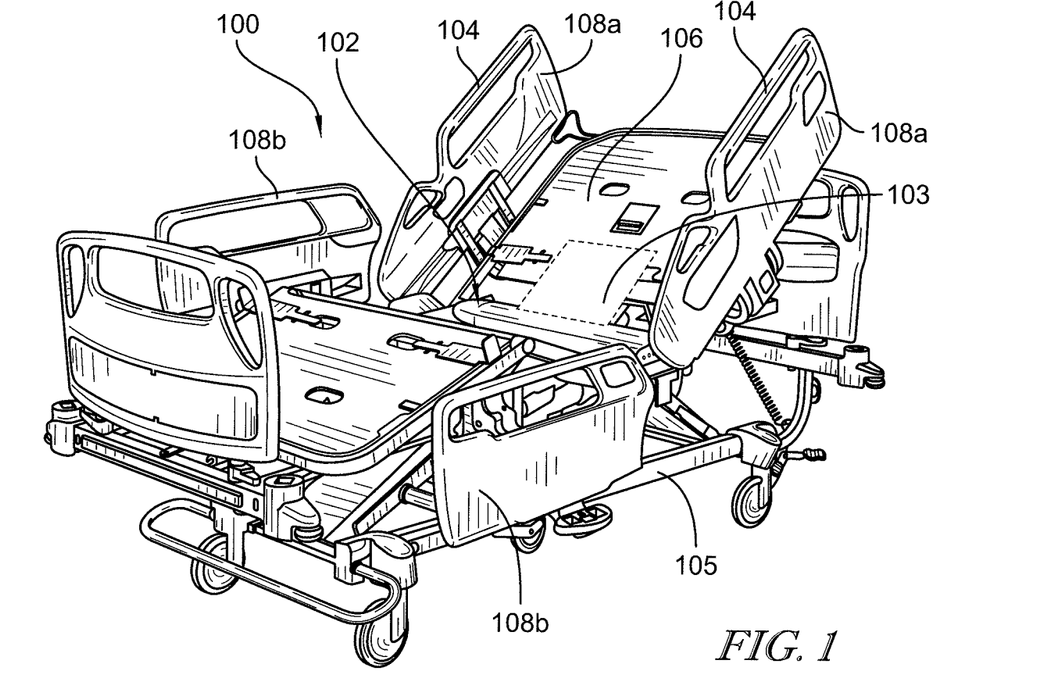
FIG. 1 shows a patient support system according to the present disclosure.
Figure 3A:
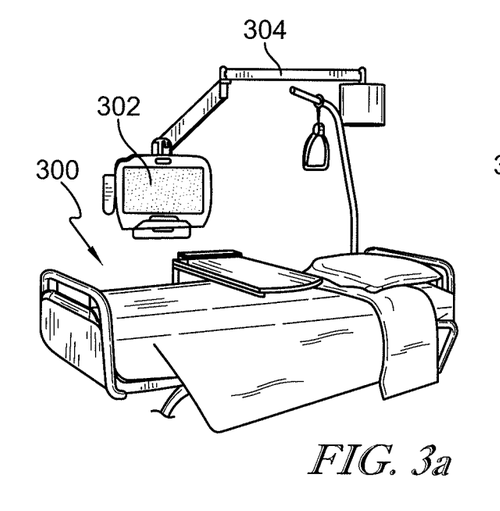
FIGS. 3(a) and 3(b) show alternative embodiments of a patient support system according to the present disclosure.
Figure 4A:
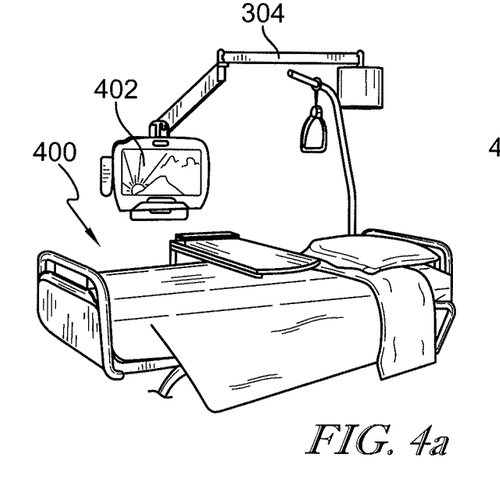
FIGS. 4(a) and 4(b) show alternative embodiments of a patient support system shown in FIGS. 3(a) and 3(b)

FIG. 1 shows a patient support system 100 comprising a base frame 102, a patient support surface 305 (see FIGS. 3(a) and 4(a)) such as a mattress, a plurality of sensors 103, a controller 107 (see FIG. 5), and light emitting devices 104. The base frame 102 comprises a lower frame 105, supports or lift mechanisms coupled to the lower frame 105, and an upper frame 106 movably supported above the lower frame by the supports. The lift mechanisms may be configured to raise and lower the upper frame 106 with respect to the lower frame 105 and move the upper frame 106 between various orientations, such as, Trendelenburg and reverse Trendelenburg.

The upper frame 106 includes an upper frame base, a deck coupled to the upper frame base, and a plurality of siderails 108. The deck may include a leg section, a thigh section, a seat section, and a head and torso section. The leg section and the thigh section define a lower limb support section. The head and torso section define an upper body support section. The leg section, the thigh section, and the seat section define a lower body support section.

The siderails 108 are configured to move between a deployed position and a storage position, and are used to locate the perimeter of the upper frame and assist with ingress/egress to/from the person support apparatus.

In this example, the light emitting devices 104 are provided on each head-end siderail 108a. The light emitting devices are configured to face the patient when the patient is on the patient support apparatus.

The person support surface 305 is preferably configured to support a person thereon and move with the deck between the various configurations. The person support surface 305 can include a heat and moisture regulating topper positioned on the mattress. The person support surface 305 may include a pressure mapping mat positioned on the mattress. The person support surface 305 preferably includes a leg portion, a thigh portion, a seat portion, and a head and torso portion, which is supported on corresponding sections of the deck.

The plurality of sensors are configured to monitor physical and physiological characteristics of the patient relating to the stage of sleep of the patient. The sensors monitor at least some of: patient movement; patient breathing rate; patient heart rate; patient temperature; and body temperature. The outputs of the sensors are transmitted to the controller, and the controller is configured to determine the stage of sleep of the patient in dependence on those sensor outputs.

As will be appreciated, the plurality of sensors may be provided on alternative portions of the patient support surface, and used alone or in combination. At least some of the sensors may be provided as part of a wearable device, such as a chest-band or vest.

The controller 107 is further configured to receive a wake-up signal. On receipt of the wake-up signal, the controller 107 initiates monitoring and determining the stage of sleep that the patient is in. Alternatively, the controller 107 may continuously monitor and determine the stage of sleep that the patient is in. After receipt of the wake-up signal, and when it is determined that the patient is in a light stage of sleep, the controller 107 activates the light emitting devices 104 to emit light substantially only in a first range of visible wavelengths between about 450 nm and about 470 nm. It has been found that such wavelengths of light suppress melatonin synthesis and thereby induce the patient to wake-up.

Figure 2:
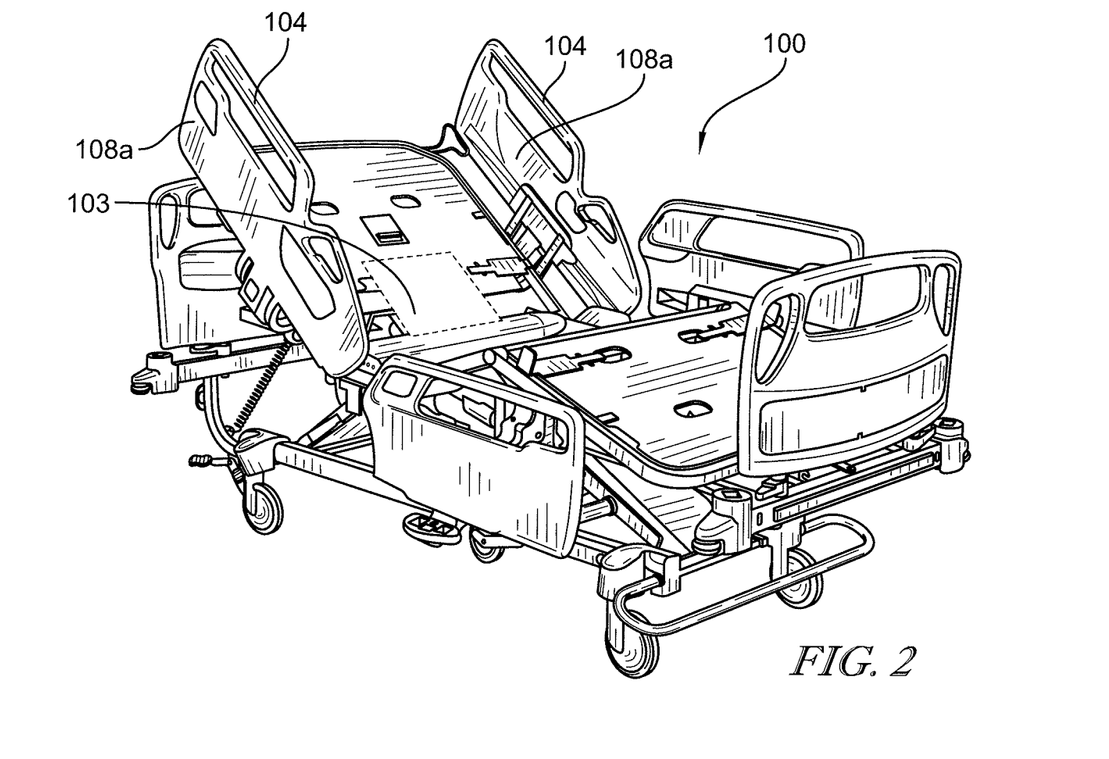
FIG. 2 shows an alternative view of the patient support system of FIG. 1.

As shown in FIG. 2, the light emitting devices 104 are also capable of emitting light substantially only in a second range of visible wavelengths greater than about 590 nm. The controller 107 is further configured to activate the light emitting devices 104 to emit light substantially only in the second range of wavelengths when the controller 107 receives a sleep signal. It has been found that wavelengths within this range avoid the suppression of melatonin, and therefore promote sleep.

The wake-up signal may be generated at a pre-determined time of day, such as a time set by the patient that they wish to wake-up. Alternatively, the wake-up signal may be generated by a central computer system. This alternative is described in further detail in relation to FIG. 5.

The sleep signal may be generated at a pre-determined time of day, such as a time set by the patient that they wish to go to sleep. Alternatively, the sleep signal may be generated by a central computer system. Again, this alternative is described in further detail in relation to FIG. 5.

Figure 3B:
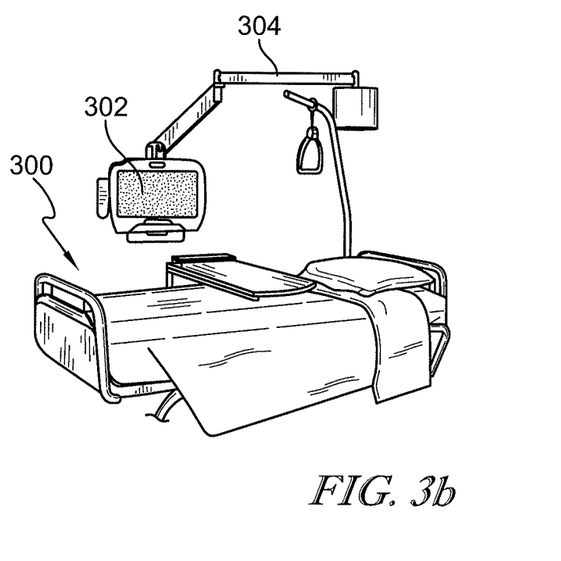
Figure 4B:
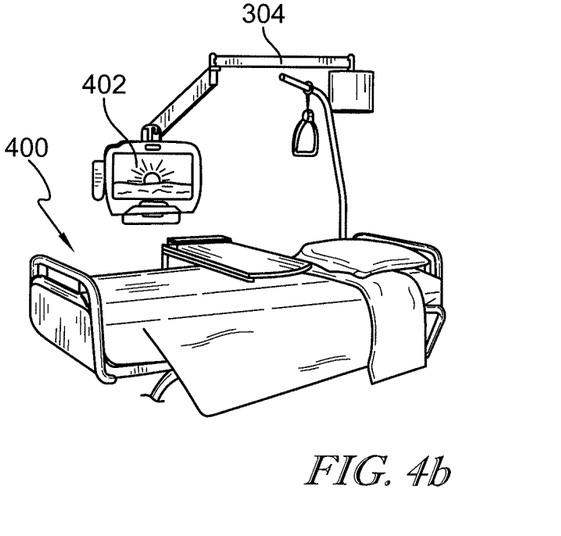

In the alternative embodiments of patient support systems 300 and 400, shown in FIGS. 3 and 4 respectively, the light emitting device is a display device 302 and 402 respectively, such as a computer monitor, multimedia device or the like. In the examples of FIGS. 3 and 4, the display device is mounted on a movable arm 304 attached to the wall. However, it will be appreciated that the display device could be coupled directly to the patient support apparatus.

In FIGS. 3(*a*) and 3(*b*), it can be seen that the display 302 is emitting light only in the first range of wavelengths and only in the second range of wavelengths respectively.

In FIGS. 4(*a*) and 4(*b*), it can be seen that the display 402 is displaying a color-adjusted image. In FIG. 4(*a*) the color-adjusted image is adjusted such that it emits lights substantially only in the first range of wavelengths, and in FIG. 4(*b*) the color-adjusted image is adjusted such that it emits lights substantially only in the second range of wavelengths. The images may be appropriate to the time of day they will be displayed. For example, the first range of wavelengths adjusted image may be a sunrise, and the second range of wavelengths adjusted image may be a sunset.

The above described examples of the present disclosure may also comprise a speaker 303 for playing sound. The controller 107 may be configured to activate the speaker 303 to play sound conducive to waking up when activating the light emitting device(s) to emit light in the first range of wavelengths, and may be configured to activate the speaker 303 to play sound conducive to going to sleep when activating the light emitting device(s) to emit light in the second range of wavelengths.

Figure 5:
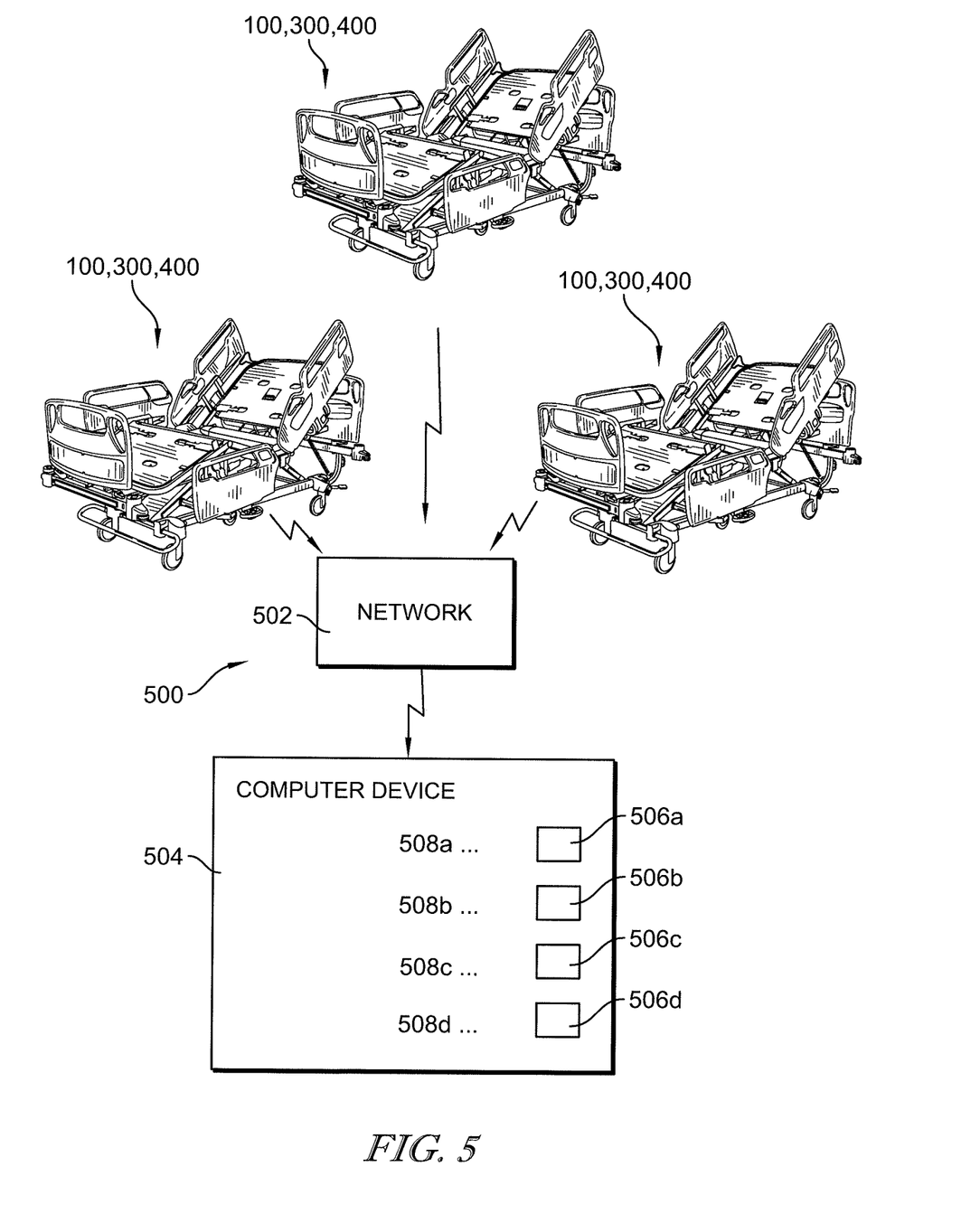
FIG. 5 shows a system according to the present disclosure.

The above described patient support systems 100, 300, 400 may be integrated into a wider system 500 in a healthcare facility such as a hospital. The system 500 is configured to enable monitoring and control of a plurality of patient's sleep experience, and to control the healthcare professional's routine. FIG. 5 shows the system 500 which comprises a plurality of patient support systems 100, 300, 400, a network 502, and a remote computer device 504. Each of the patient support systems 100, 300, 400 further comprises communications circuitry 109 configured to enable electronic communications. The computer device 504 also comprises communications circuitry 509.

The network 502 is configured to enable communications between each of the patient support systems 100, 300, 400 and the remote computer device 504. The communications may be over a wired or wireless communications link.

The remote computer device 504 is configured to receive an input from a user, such as a healthcare professional, to initiate a wake-up process. The input may be received on a touchscreen, via a physical input such as a computer mouse, or the like. After receipt of the input initiating the wake-up process, the computer device 504 communicates with each patient support system 100, 300, 400 over the network 502. The computer device 504 requests stage of sleep data for each patient associated with each of the plurality of patient support systems 100, 300, 400. When the computer device receives the stage of sleep data for each patient, it sends a wake-up signal to each patient support system 100, 300, 400 where the associated patient is in a light stage of sleep. On receipt of the wake-up signal the patient support system 100, 300, 400 operates as described above. The computer device 504 then indicates to the user the patient support systems 100, 300, 400 which were sent a wake-up signal. The computer device 504 also displays an indication of which patients are awake, and which are asleep. For example via lights 506*a*, 506*b*, 506*c*, and 506*d*, adjacent which are patient identifier information 508*a*, 508*b*, 508*c* and 508*d*, respectively. The remote computer device 504 comprises a controller 507 which is configured to be the controller for each of the plurality of patient support systems 100, 300, 400 in some embodiments.

Figure 6:
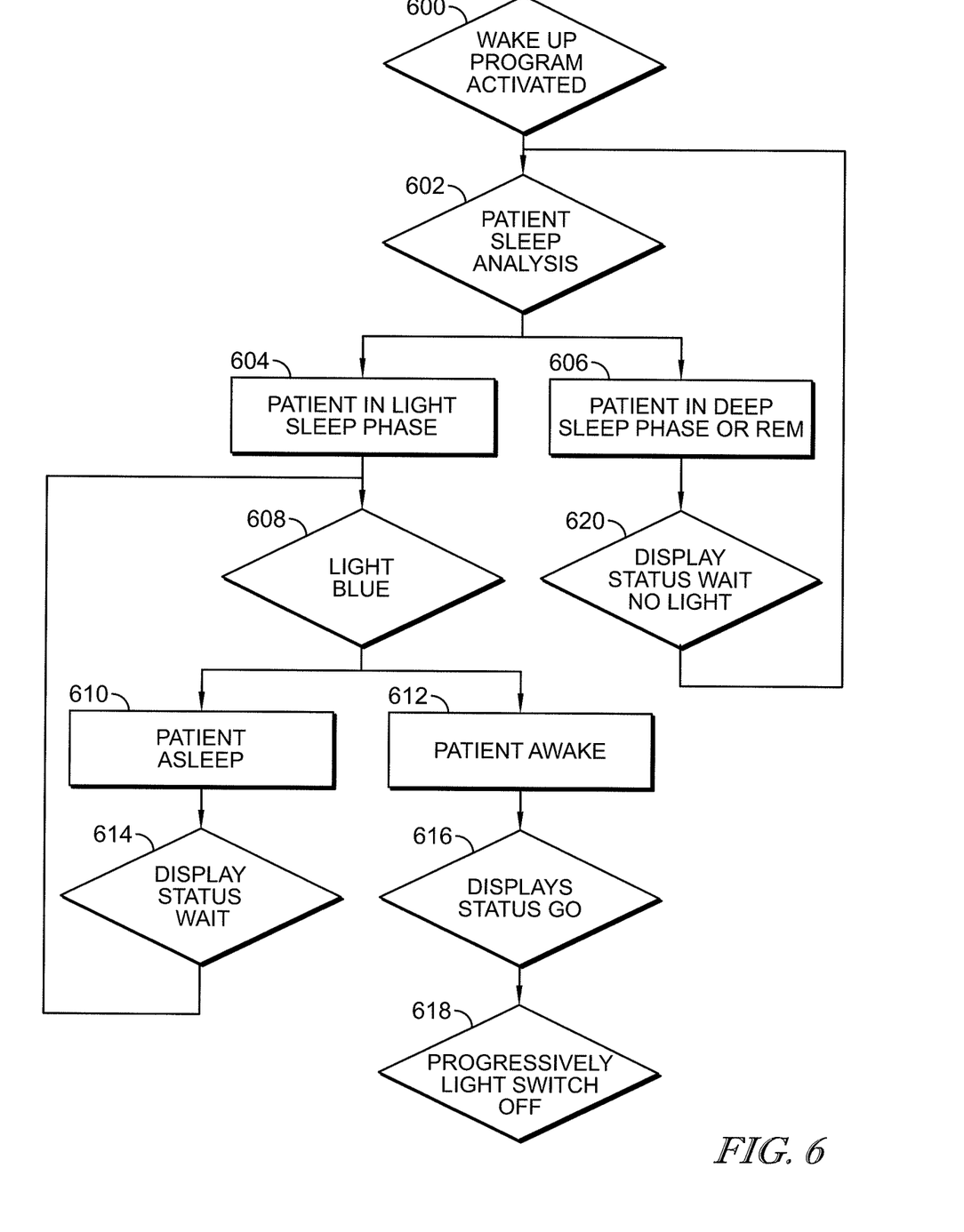
FIG. 6 shows a flow diagram of the wake-up process carried out by the system shown in FIG. 5.

FIG. 6 shows a flow diagram of the wake-up process initiated and carried out by the computer device 504. As can be seen, on initiation of the wake-up process 600, the computer device conducts the sleep stage determination 602, for each patient associated with a patient support system. The patient will either be in a light stage of sleep 604, including awake, or a deep sleep stage, including REM 606. If the patient is in a light stage of sleep the light emitting device on the respective patient support system 100, 300, 400 is activated 608. While the patient remains asleep 610, an indicator is displayed on the computer device 504 indicating that the healthcare professional should wait before attending that patient. When the patient awakes 612, an indicator is displayed on the computer device 504 to indicate that the patient is awake and the healthcare professional can attend to that patient. The light emitting device is then progressively turned off 618.

If the patient is in a deep sleep stage 606, then the system continues to communicate 620 with the patient support system 100, 300, 400 until the patient is in a light stage of sleep. No indicator is provided.

The computer device 504 is configured to indicate to the user, such as a healthcare professional, the most efficient order in which to attend to the patients. The order is determined by reviewing the sleep status of each patient, and beginning with the patient who has been awake the longest, or is most likely to awake first.

The disclosure has been exemplified above by reference to FIGS. 1 to 6, where the patient support apparatus 100, 300, 400 is a hospital bed. However, it will be appreciated that the patient support apparatus may be any suitable apparatus, and according to the disclosure may comprise other forms of support apparatus.

Although certain illustrative embodiments have been described in detail above, variations and modifications exist within the scope and spirit of this disclosure as described and as defined in the following claims.

The invention claimed is:

1. A patient support system comprising a patient support apparatus having a base frame, an upper frame supported above the base frame and movable between Trendelenburg and reverse Trendelenburg orientations, and a mattress supported on the upper frame, the system further comprising:
   at least one sensor located on the upper frame beneath the mattress, configured to detect at least one of: patient movement; patient breathing rate; or patient heart rate and to produce an output;
   at least one light emitting device capable of emitting light in at least a first range of visible wavelengths between about 440 nm and about 490 nm; wherein the at least one light emitting device comprises a touchscreen of a display; and
   a controller configured to:
   receive the or each output from the at least one sensor;
   determine a stage of sleep of a patient on the mattress in dependence on the or each received output;
   receive a wake-up signal; and
   after receipt of the wake-up signal, activate the or each light emitting device to emit light substantially only in the first range of visible wavelengths when the controller next determines that the patient is in a light stage of sleep.

2. The patient support apparatus according to claim 1, wherein the controller is further configured to activate the or each light emitting device to emit light substantially only in the first range of visible wavelengths by progressively increasing the intensity of the light emitted by the or each light emitting device from a first intensity to a second intensity over a pre-determined period of time.

3. The patient support apparatus according to claim 1, wherein the at least one light emitting device is further capable of emitting light in at least a second range of visible wavelengths greater than about 590 nm, wherein the controller is further configured to:
   receive a sleep signal; and
   after receipt of the sleep signal, activate the or each light emitting device to emit light substantially only in the second range of visible wavelengths to promote an onset of sleep.

4. The patient support apparatus according to claim 3, wherein the controller is further configured to deactivate the or each light emitting device from emitting light in the second range of visible wavelengths when the controller determines that the patient is in a stage of sleep.

5. The patient support apparatus according to claim 1, wherein the controller is further configured to deactivate the or each light emitting device from emitting light in the first range of visible wavelengths when the controller determines that the patient's stage of sleep is awake.

6. The patient support apparatus according to claim 1, wherein the wake-up signal is at least one of: a signal generated at a pre-determined time of day or a signal generated by a remote user request to wake-up the patient.

7. The patient support apparatus according to claim 1, wherein the or each light emitting device is coupled to the base frame, adjacent a head-end of the mattress.

8. The patient support apparatus according to claim 1, wherein the at least one light emitting device is coupled to a wall adjacent the patient support apparatus.

9. The patient support apparatus according to claim 8, wherein the controller is configured to color-adjust an image such that, when the color-adjusted image is displayed on the display device, the display substantially only emits light in the first range of wavelengths.

10. The patient support apparatus according to claim 1, further comprising a speaker, wherein the controller is further configured to activate the speaker to output sound conducive to waking up, when activating the or each light emitting device to emit light substantially only in the first range of visible wavelengths.

11. A system for a healthcare facility, comprising:
   a plurality of patient support systems, each patient support system being configured according to claim 1, each patient support system further comprising communications circuitry configured to communicate with a network; and
   a computer device remote from the patient support systems, comprising communications circuitry configured to communicate with the network, the computer device configured to:
   receive an input from a user to initiate a wake-up process;
   request stage of sleep data for each patient associated with each of the plurality of patient support systems;
   receive the stage of sleep data for each patient;
   send a wake-up signal to each patient support system where the associated patient is in a light stage of sleep; and
   indicate to the user the patient support systems which were sent a wake-up signal.

12. The system according to claim 11, wherein the computer device is further configured to periodically request stage of sleep data for each patient associated with each of the plurality of patient support systems until a wake-up signal has been sent to all of the plurality of patient support systems.

13. The system according to claim 11, wherein the computer device is further configured to indicate to the user the patient support systems where the associated patient's determined stage of sleep is awake.

14. The system according to claim 11, wherein the computer device is further configured to:

determine a linear sequence, in which to attend the patients, in dependence on the stage of sleep data received from each patient support system, the sequence starting with the patient whose stage of sleep has been awake for the longest period of time; and
indicate the sequence to the user.

15. The system according to claim 11, wherein the remote computer device comprises the controller for each of the plurality of patient support systems.

16. A system for a healthcare facility, the system comprising
a plurality of patient support systems, each patient support system comprising
a patient support apparatus having a base frame, an upper frame supported above the base frame and movable between Trendelenburg and reverse Trendelenburg orientations, and a mattress supported on the upper frame,
at least one sensor located on the upper frame beneath the mattress and configured to produce at least one output,
at least one light emitting device capable of emitting light in at least a first range of visible wavelengths between about 440 nm and about 490 nm;
a controller configured to:
receive the or each output from the at least one sensor;
determine a stage of sleep of a patient on the mattress in dependence on the or each received output;
receive a wake-up signal; and
after receipt of the wake-up signal, activate the or each light emitting device to emit light substantially only in the first range of visible wavelengths when the controller next determines that the patient is in a light stage of sleep; and
first communications circuitry configured to communicate with a network; and
a computer device remote from the patient support systems, comprising second communications circuitry configured to communicate with the network, the computer device configured to:
receive an input from a user to initiate a wake-up process;
request stage of sleep data for each patient associated with each of the plurality of patient support systems;
receive the stage of sleep data for each patient;
send a wake-up signal to each patient support system but only where the associated patient is in a light stage of sleep; and
indicate to the user the patient support systems which were sent a wake-up signal.

17. The system according to claim 16, wherein the computer device is further configured to periodically request stage of sleep data for each patient associated with each of the plurality of patient support systems until a wake-up signal has been sent to all of the plurality of patient support systems.

18. The system according to claim 16, wherein the computer device is further configured to indicate to the user the patient support systems where the associated patient's determined stage of sleep is awake.

19. The system according to claim 16, wherein the computer device is further configured to:
determine a linear sequence, in which to attend the patients, in dependence on the stage of sleep data received from each patient support system, the sequence starting with the patient whose stage of sleep has been awake for the longest period of time; and
indicate the sequence to the user.

20. The system according to claim 16, wherein the remote computer device comprises the controller for each of the plurality of patient support systems.

* * * * *